(12) United States Patent
Strobl

(10) Patent No.: US 10,010,366 B2
(45) Date of Patent: Jul. 3, 2018

(54) SURGICAL DEVICES AND METHODS FOR TISSUE CUTTING AND SEALING

(71) Applicant: Ethicon Endo-Surgery, Inc., Cincinnati, OH (US)

(72) Inventor: Geoffrey S. Strobl, Williamsburg, OH (US)

(73) Assignee: Ethicon LLC, Guaynabo, PR (US)

( * ) Notice: Subject to any disclaimer, the term of this patent is extended or adjusted under 35 U.S.C. 154(b) by 688 days.

(21) Appl. No.: 14/573,074

(22) Filed: Dec. 17, 2014

(65) Prior Publication Data

US 2016/0175025 A1    Jun. 23, 2016

(51) Int. Cl.
| | |
|---|---|
| A61B 18/18 | (2006.01) |
| A61B 18/14 | (2006.01) |
| A61B 18/00 | (2006.01) |
| A61B 18/16 | (2006.01) |

(52) U.S. Cl.
CPC .. *A61B 18/1445* (2013.01); *A61B 2018/0063* (2013.01); *A61B 2018/00071* (2013.01); *A61B 2018/00708* (2013.01); *A61B 2018/162* (2013.01)

(58) Field of Classification Search
CPC ...... A61B 18/1445; A61B 2018/00071; A61B 2018/0063; A61B 2018/00708; A61B 2018/162

See application file for complete search history.

(56) References Cited

U.S. PATENT DOCUMENTS

| 4,814,244 A | * | 3/1989 | Koguchi | G03F 7/2024 204/192.34 |
|---|---|---|---|---|
| 7,585,310 B2 | * | 9/2009 | Phan | A61B 17/29 606/207 |
| 8,574,229 B2 | * | 11/2013 | Eder | A61B 18/1442 606/207 |
| 2006/0030122 A1 | * | 2/2006 | Shimoda | G02F 1/13454 438/455 |

OTHER PUBLICATIONS

Stephenson, Andrew P. et al., "A Tunable Metal-Organic Resistance Thermometer," ChemPhysChem, vol. 12 (2011):116-121.

* cited by examiner

*Primary Examiner* — George Manuel
(74) *Attorney, Agent, or Firm* — Mintz Levin Cohn Ferris Glovsky and Popeo, P.C.

(57) ABSTRACT

Surgical devices and methods are described herein that provide energy density control during tissue sealing. In general, these devices include a handle portion, an elongate shaft, and an end effector having a first jaw having a first tissue engaging surface and a second jaw having a second tissue engaging surface. The first tissue engaging surface can include an energy delivering electrode having a selected pattern of varying conductivity which may include a discrete region or a continuous pattern. The energy delivering electrode may be formed from a polymer substrate that includes a metal. The metal may be mixed into the substrate using an ion beam process. The amount of ions in the ion beam, the energy of the ion beam, or both may be varied to create the selected pattern of varying conductivity.

12 Claims, 12 Drawing Sheets

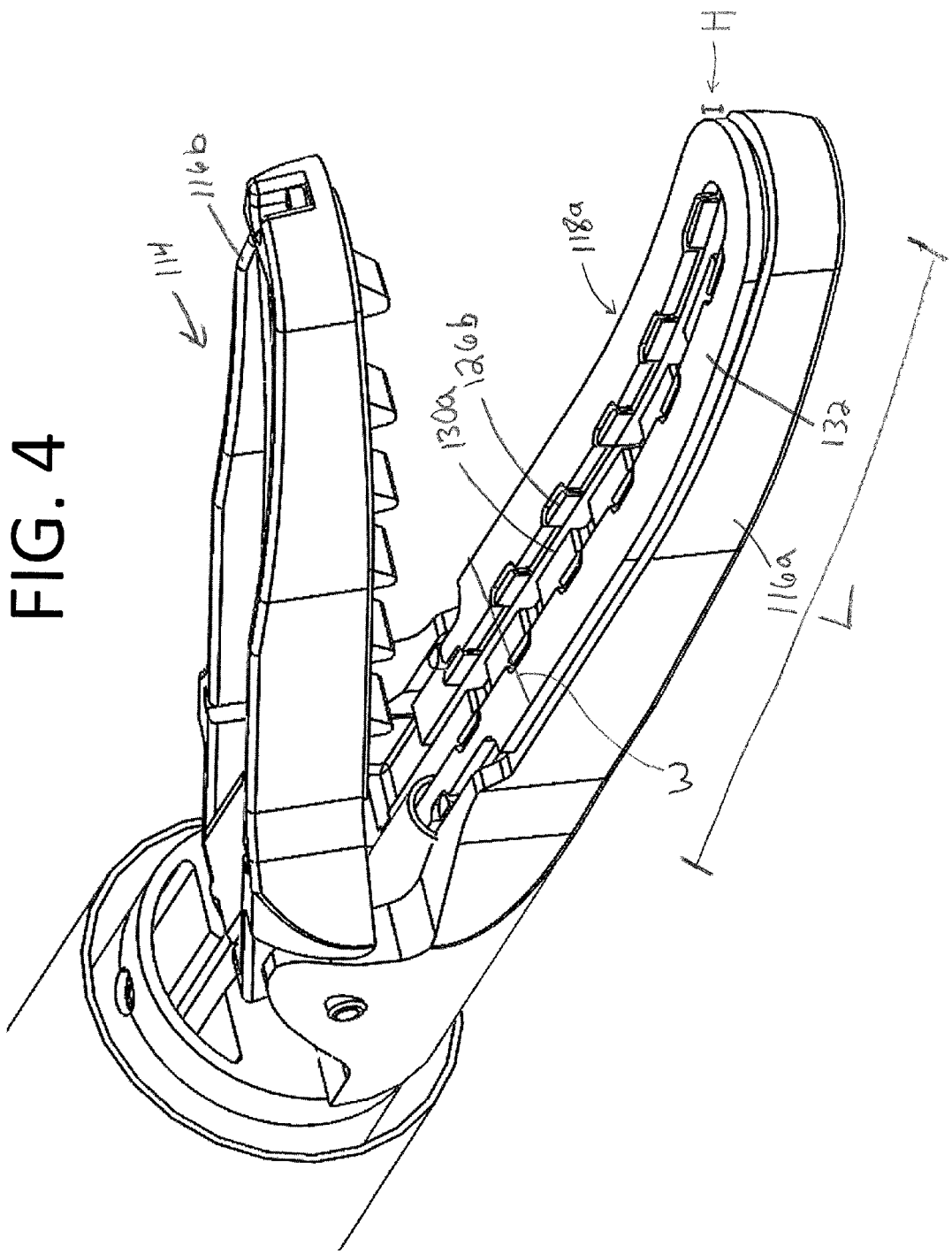

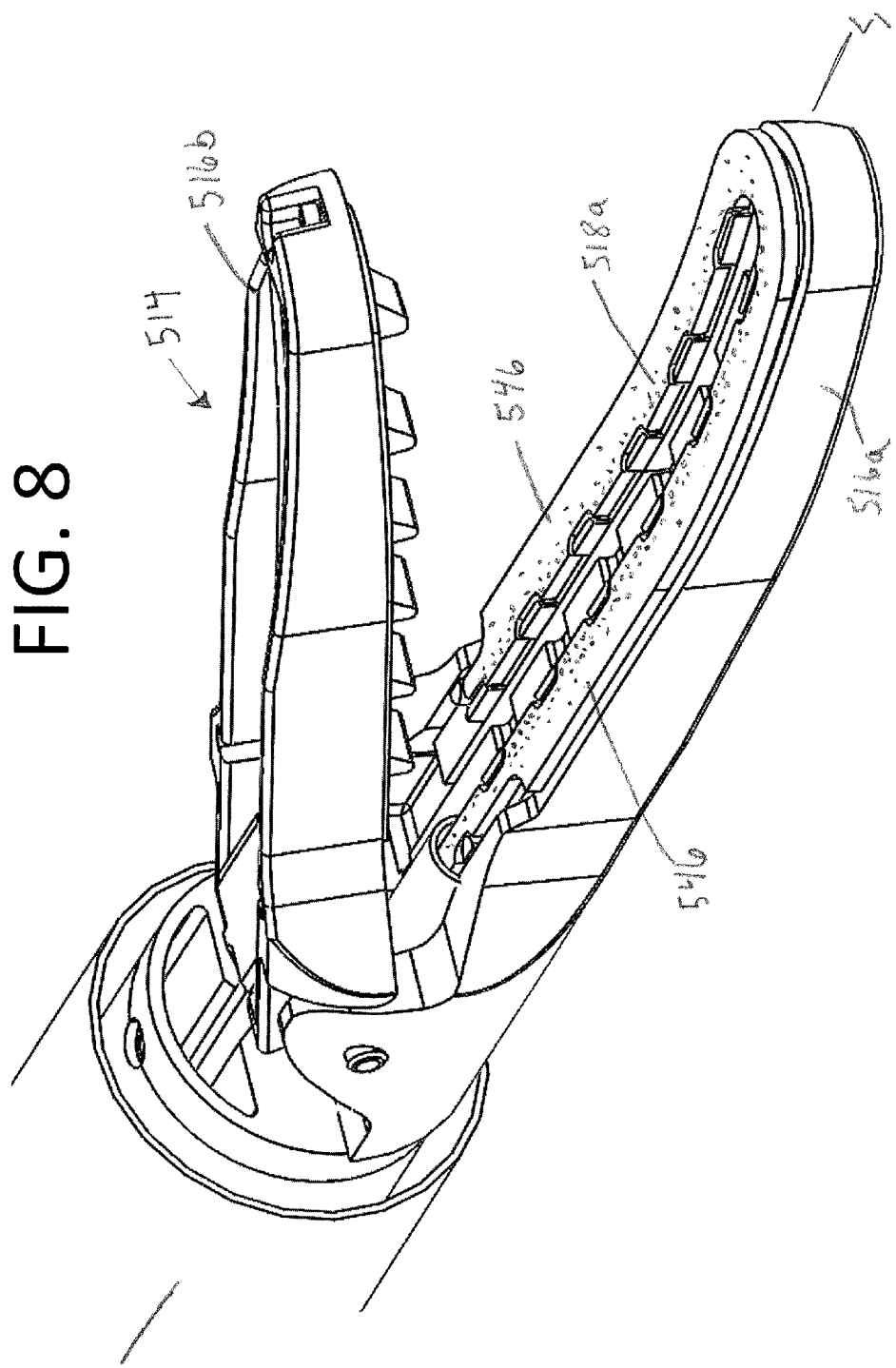

SURGICAL DEVICES AND METHODS FOR TISSUE CUTTING AND SEALING

FIELD

The present disclosure relates to surgical devices and methods of making such devices and, more particularly, to surgical devices for cutting and sealing tissue that provide energy density control and methods of making such devices.

BACKGROUND

Various surgical devices are known for compressing and cutting different types of tissue. In general, these devices have an end effector, such as a pair of opposed jaw members, configured to engage tissue and a cutting mechanism that is configured to sever tissue engaged by the end effector. Certain of these devices can also be configured to apply energy, such as radio frequency (RF) electrical energy, to the tissue disposed between the jaws. The application of electrical energy in the vicinity of a tissue cut can seal the cut to prevent bleeding of the tissue and leakage of other fluids through the cut.

A common concern when using any of these devices is achieving hemostasis so that bleeding of the target tissue is limited. Energy density and tissue compression are factors in achieving hemostasis. High energy density can heat tissue too quickly resulting in excessive steam generation and/or charring of the tissue, while low energy density increases cycle time or may fail to heat the tissue to an adequate temperature to achieve a seal. By increasing the amount of pressure applied to the target tissue, the flow of blood can be limited, thereby decreasing the time necessary to achieve hemostasis. However, applying too much pressure can result in an unnecessary reduction in blood flow to the tissue surrounding the cut-line, potentially resulting in an elevated level of necrosis, a slower rate of healing, and/or a greater recovery period. Excessive compression can also mechanically separate or damage tissue preventing a seal. Inadequate compression will not approximate the two opposing sides of a vessel to achieve the seal. In a RF device in which jaw movement is about a pivot, the compressive force proximal to the pivot is greater than at a distal location which results in variation in energy density and tissue compression and thus inconsistent tissue sealing.

Accordingly, there remains a need for surgical devices and methods for energy density control during a tissue sealing process to improve seal consistency.

SUMMARY

The devices and methods described herein address the aforementioned need by providing an energy delivering electrode having a selected pattern of varying conductivity to adjust energy density across the profile of the electrode during tissue sealing. In certain embodiments, the energy delivering electrode is disposed on a tissue engaging surface of an end effector of a surgical tool.

In one embodiment, the surgical device includes a handle portion and an elongate shaft having a proximal end and a distal end. The proximal end of the elongate shaft is operatively coupled to the handle portion. The surgical device also includes an end effector at the distal end of the shaft. The end effector includes a first jaw having a first tissue engaging surface and a second jaw having a second tissue engaging surface facing the first tissue engaging surface. The surgical device includes an actuator configured to approximate the first jaw and the second jaw. One of the first and second tissue engaging surfaces includes an energy delivering electrode having a selected pattern of varying conductivity.

The device may vary in any number of ways. The device may include a return electrode electrically isolated from the energy delivering electrode. The device can include a switch mechanism configured to selectively deliver energy to the energy delivering electrode. In one aspect, the energy delivering electrode may have a substantially uniform thickness throughout its width and length. The energy delivering electrode can be formed of a polymer substrate that includes a metal.

The selected pattern may also have any number of variations. The selected pattern can be a discrete region of varying conductivity or a continuous pattern of varying conductivity. The selected pattern can be a gradient of conductivity that extends from a distal end to a proximal end of the energy delivering electrode or extends radially from the longitudinal axis to the outer edges of the energy delivering electrode. In one embodiment, the distal end of the first tissue engaging surface is more conductive than the proximal end of the energy delivering electrode.

In another embodiment, a surgical device includes an end effector comprising a first jaw having a first tissue engaging surface and a second jaw having a second tissue engaging surface facing the first tissue engaging surface. The first tissue engaging surface includes an energy delivering electrode formed of a polymer substrate that includes a metal. The energy delivering electrode has a gradient of conductivity configured to control energy density along the energy delivering electrode in a desired manner so as to obtain a consistent tissue seal along the length of the first tissue engaging surface when tissue is clamped between the first and second jaws and energy is applied to the first tissue engaging surface.

The device may vary in any number of ways. The end effector may include a return electrode electrically isolated from the energy delivering electrode. The energy delivering electrode and the return electrode may be operatively coupled to an energy source.

The energy delivering electrode also may vary in any number of ways. The energy delivering electrode may have a substantially uniform thickness throughout its width and length. The selected pattern may be a gradient of conductivity that extends from a distal end to a proximal end of the energy delivering electrode or extends radially from a longitudinal axis to outer edges of the energy delivering electrode. The distal end of the first tissue engaging surface may be more conductive than the proximal end of the energy delivering electrode. In one embodiment, the metal includes a tin/antimony alloy.

In another aspect, a method of making an electrode for a surgical tool, where the electrode has a selected pattern of varying conductivity, includes depositing a film comprising a metal on a polymer substrate, and applying an ion beam to the film in a desired manner to form the selected pattern of varying conductivity. Applying an ion beam to the film in a desired manner may include varying the amounts of ions in the ion beam, varying the ion beam energy, or a combination thereof to form the selected pattern of varying conductivity.

The method may have any number of variations. The film can be deposited using a vapor deposition process. The selected pattern may include a gradient of conductivity that extends from a distal end to a proximal end of the energy delivering electrode or extends radially from a longitudinal axis to outer edges of the energy delivering electrode.

BRIEF DESCRIPTION OF DRAWINGS

The present devices and methods will be more fully understood from the following detailed description taken in conjunction with the accompanying drawings, in which:

FIG. 4 is a perspective view of one embodiment of an end effector;

FIG. 8 is a perspective view of a further embodiment of an end effector having a continuous pattern of conductivity on an electrode.

DETAILED DESCRIPTION

Figure 1:
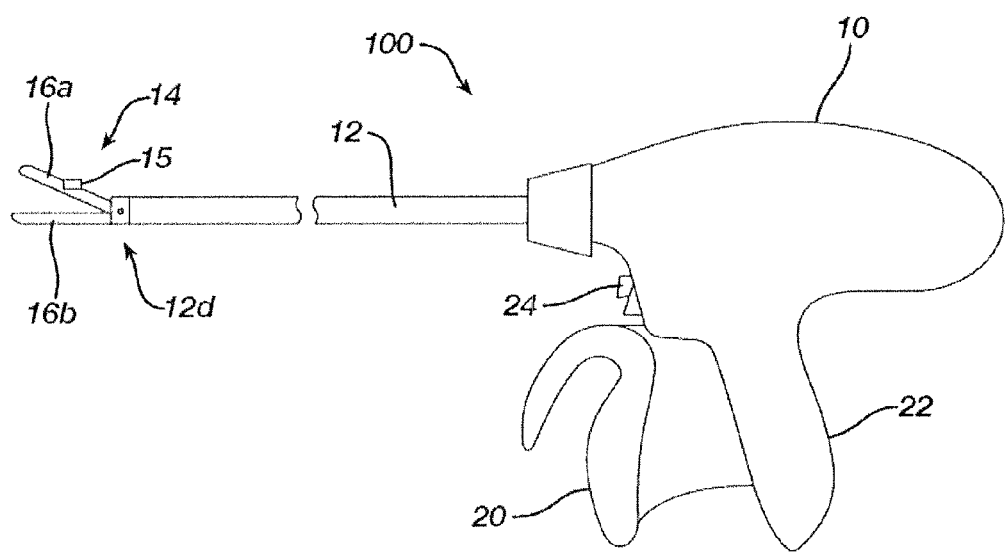
FIG. 1 is a side view illustration of one embodiment of a powered surgical device.

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present device and methods is defined solely by the claims. The features illustrated or described in connection with one exemplary embodiment may be combined with the features of other embodiments. Such modifications and variations are intended to be included within the scope of the present disclosure.

Further, in the present disclosure, like-numbered components of the embodiments generally have similar features, and thus within a particular embodiment each feature of each like-numbered component is not necessarily fully elaborated upon. Additionally, to the extent that linear or circular dimensions are used in the description of the disclosed devices and methods, such dimensions are not intended to limit the types of shapes that can be used in conjunction with such devices and methods. A person skilled in the art will recognize that an equivalent to such linear and circular dimensions can easily be determined for any geometric shape. Sizes and shapes of the devices, and the components thereof, can depend at least on the anatomy of the subject in which the devices will be used, the size and shape of components with which the devices will be used, and the methods and procedures in which the devices will be used.

Various surgical devices and methods are provided for energy density control during a tissue sealing process. As explained below, the devices and methods described herein generally provide greater energy density control by having an energy delivering electrode that is disposed on a tissue engaging surface of a surgical device and has a selected pattern of varying conductivity. In certain embodiments, the selected pattern is a discrete or a continuous pattern of varying conductivity. In other embodiments, the selected pattern is a gradient of conductivity. The energy delivering electrode can be formed by applying a film of metal to a polymer substrate and applying an ion beam to the film to mix the metal into the polymer. By varying the parameters of the ion beam, the selected pattern of varying conductivity is formed. In use, these surgical devices can apply energy to tissue and control energy density to achieve a more consistent tissue seal and achieve hemostasis.

A person skilled in the art will understand that the electrode structure disclosed herein is applicable to a variety of surgical devices that can effect cutting and/or sealing of tissue. Exemplary surgical devices include those that are bipolar as well as those that are monopolar. In general, the surgical devices described herein include an elongate shaft having a proximal end and a distal end. Optionally, a proximal end of the elongate shaft can be operatively coupled to a handle. In one aspect, the surgical device includes an end effector at the distal end of the shaft. The end effector can include a first jaw and a second jaw configured to engage tissue therebetween. The surgical device includes an actuator configured to approximate or close the first jaw and the second jaw by moving one or both of the jaws towards each other. The first jaw has a first tissue engaging surface and the second jaw has a second tissue engaging surface facing the first tissue engaging surface. At least one of the tissue engaging surfaces includes an energy delivering electrode having a selected pattern of varying conductivity which is described in more detail below. In some embodiments, the end effector may be incorporated into a surgical system in which it is attached to an arm or another structure that enables manipulation of the end effector directly by a surgeon (e.g., by manipulating the device through a handle attached to the shaft) or through a surgical system, such as a robotic surgical system.

A person skilled in the art will understand that the electrode structure disclosed herein, with a variable pattern of conductivity, is applicable to a variety of surgical devices. FIG. 1 illustrates one embodiment of a surgical device that includes the electrode structure disclosed herein, having a variable pattern of conductivity and configured to grasp, cut, and seal tissue. As shown, surgical device 100 includes a handle portion 10, an elongate shaft 12 having a proximal end that is operatively coupled to the handle portion 10, and an end effector 14 having a first jaw 16a and second jaw 16b for grasping tissue at the distal end of the shaft 12. A person skilled in the art will appreciate that the shaft can be removably and replaceably attached to the handle, or it can be non-removably attached to the handle. The handle portion 10 can be any type of pistol-grip or other type of handle known in the art that is configured to carry various actuators, such as actuator levers, triggers or sliders for actuating the end effector 14. The surgical device may include a closure actuator or closure grip that can be configured to open and close the jaws of the end effector. In the illustrated embodiment, the handle portion 10 includes a closure grip 20 and a stationary grip 22, and movement of the closure grip 20 toward and away from the stationary grip 22 adjusts the relative position of the jaws 16a, 16b. The shaft 12 extends distally from the handle portion 10 and can have a bore (not shown) extending therethrough for carrying mechanisms for actuating the jaws 16a, 16b.

Although not illustrated in FIG. 1, the surgical device 100 can include, or be connected to, an energy source (such as a source of RF energy) to deliver energy to tissue through one or more electrodes disposed on end effector 14. Also, the device can include a switch mechanism 24 configured to selectively deliver energy to the energy delivering electrode. For example, the switch mechanism can be a firing actuator that can be moved to apply energy to the electrode. In one aspect, the device can be powered by a battery, which can be housed within handle portion 10.

Figure 2:
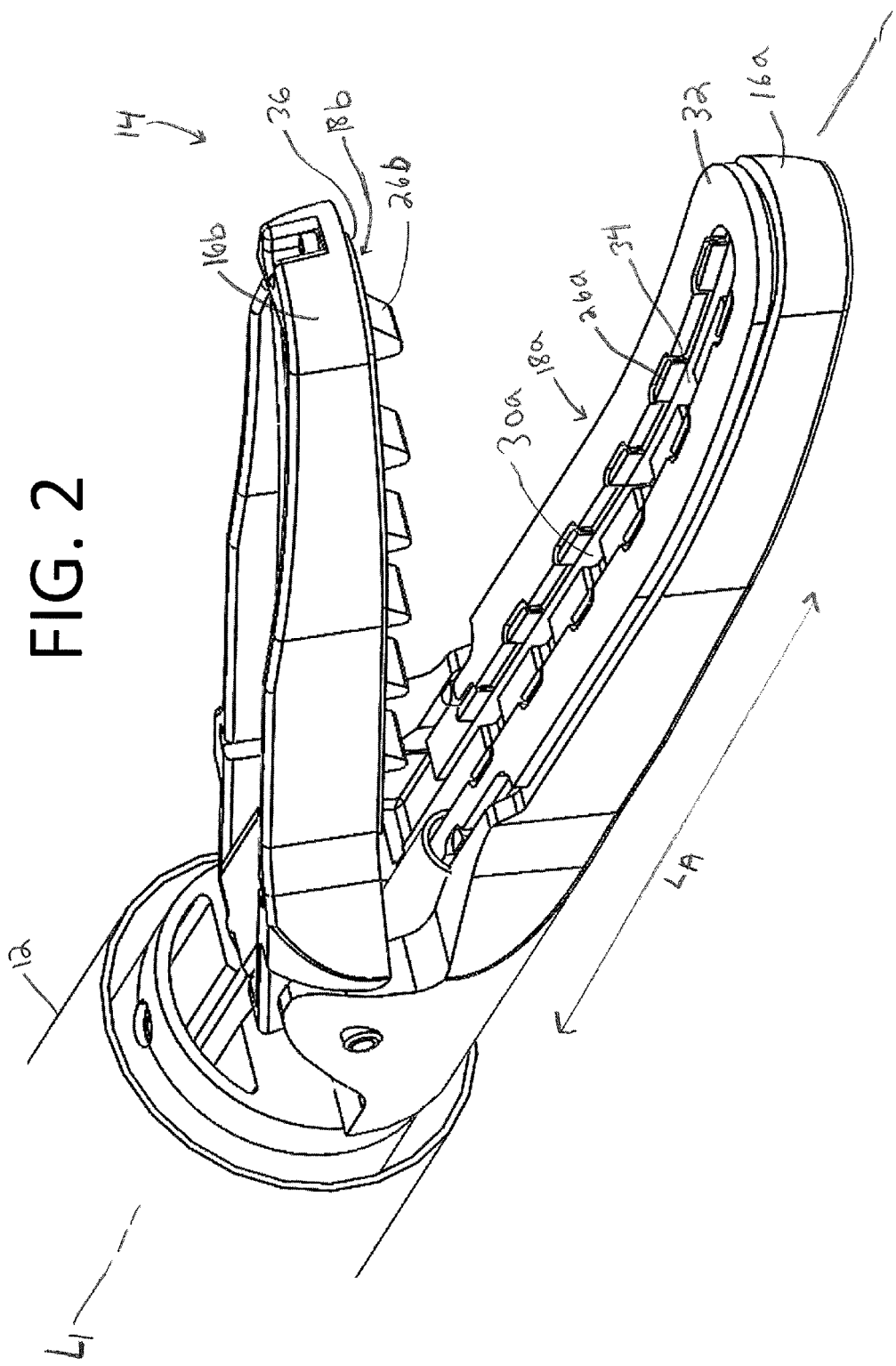
FIG. 2 is a perspective view illustration of an end effector of a surgical device in an open position.

The end effector can have a variety of sizes, shapes, and configurations. By way of example and as shown in FIG. 2, the end effector 14 includes a first, lower jaw 16a and second, upper jaw 16b, one or both of which are configured to close or approximate about an axis. Both of the jaws 16a, 16b can be moveable relative to the shaft 12 or, alternatively, a single jaw can rotate so that the end effector 14 can move between a first, open position in which the jaws 16a, 16b are positioned at a distance apart to a second, closed position in which the jaws 16a, 16b are moved toward one another and are substantially opposed and closed. When the jaws 16a, 16b are in the second, closed position, the opposed tissue engaging surfaces of the first and second jaws are substantially parallel, and the jaws 16a, 16b are in direct contact. In the illustrated embodiment, the upper jaw 16b can pivot relative to the shaft 12 and relative to the lower jaw 16a while the lower jaw 16a remains stationary. In the illustrated embodiment shown in FIG. 2, the jaws 16a, 16b have a substantially elongate and curved shape long axis $L_1$ but a person skilled in the art will appreciate that one or both of the jaws 16a, 16b can be substantially straight along axis $L_1$. The jaws 16a, 16b can have any suitable axial length $L_A$ for engaging tissue, where the axial length $L_A$ is measured along a longitudinal axis $L_1$ of the end effector 14, as shown in FIG. 2. The axial length $L_A$ of the jaws 16a, 16b can also be selected based on the targeted anatomical structure for transection and/or sealing.

The jaws may be made of any material suitable for biomedical applications and known to those skilled in the art. The jaws can be made of a metallic material, however all or part of the jaws may include a ceramic or a plastic. As described below, the jaws have one or more electrodes for delivering electrical current to tissue to effect cutting and/or sealing of tissue. In a bipolar mode, one or both of the jaws can include an energy delivering electrode as described herein and a return electrode. The return electrode is electrically isolated from the energy delivering electrode. Also, the energy delivering electrode and the return electrode are operatively coupled to an energy source, such as an RF energy source. In a monopolar mode, one or both jaws include only an energy delivering electrode as described herein and a ground pad is placed on a patient's body to complete the electrical circuit.

The jaws can have any combination of features configured to facilitate grasping tissue therebetween. For example, the first jaw 16a has a first tissue engaging surface and the second jaw 16b has a second tissue engaging surface. As shown in FIG. 2, the first jaw 16a has an inner, first tissue engaging surface 18a and the second jaw 16b has an inner, second tissue engaging surface 18b, both of the first and second tissue engaging surfaces 18a, 18b being configured to directly contact tissue. The tissue engaging surfaces can have any desired dimensions. In an embodiment, the width of the first tissue engaging surface is constant along the length of the first tissue engaging surface, although the width may vary.

Either one or both of the tissue engaging surfaces 18a, 18b can include one or more surface features formed thereon that can assist in grasping the tissue. For example, the surface features can include various formations, such as teeth, ridges, depressions, or other gripping elements configured to increase friction between the tissue and the first and second tissue engaging surfaces 18a, 18b of the jaws 16a, 16b without tearing or otherwise damaging the tissue in contact with such surface features. FIG. 2 illustrates a plurality of teeth 26a, 26b positioned along an axial length of both of the tissue engaging surfaces 18a, 18b that can facilitate grasping of tissue. The device can also include elevated portions on at least one of the tissue engaging surfaces. For example, tissue engaging surfaces may include elevated bumps, posts, or other boss shapes having properties of an insulator to provide contact points to ensure jaw gap spacing.

The first and second jaws may have other features. For example, the first and second jaws 16a, 16b can optionally include features for interacting with a compression member (not shown) configured to apply compressive forces on tissue. The first and second jaws 16a, 16b can include first and second recessed slots that can receive portions of a compression member and act as a track to direct movement of the compression member. As another example, the first and second recessed slots can be configured to receive portions of a cutting element. The cutting element can be configured to transect or cut various thicknesses and types of tissue captured between the jaws.

In one embodiment, the first tissue engaging surface of the first jaw 16a includes an electrode such as an energy delivering electrode. An insulator can be positioned within a base member of the first jaw to electrically insulate the base member and the gripping elements or teeth from the energy delivering electrode, which may be positioned on top of the insulator. The second jaw 16b may also include an insulator, as appropriate, to electrically isolate portions of the energy delivering electrode. In one embodiment, the second jaw 16b can include a Positive Temperature Coefficient (PTC) insert 36 (FIG. 3B) explained in more detail below, which is connected to a first polarity via a return path for the energy source and thus acts as a return electrode. Appropriate insulators may be placed on second jaw 16b to insulate the PTC return electrode insert 36 from other components of jaw 16b. FIG. 2 shows an embodiment in which the lower, first jaw 16a has a first tissue engaging surface 18a, and an electrode 32 positioned on an insulator 34. The insulator 34 can be a ceramic insert. FIGS. 3A-3E depict various components of the first and second jaws 16a, 16b shown in FIG. 2, which form an end effector of an exemplary surgical tool with which the electrode described herein can be used.

Figure 3A:
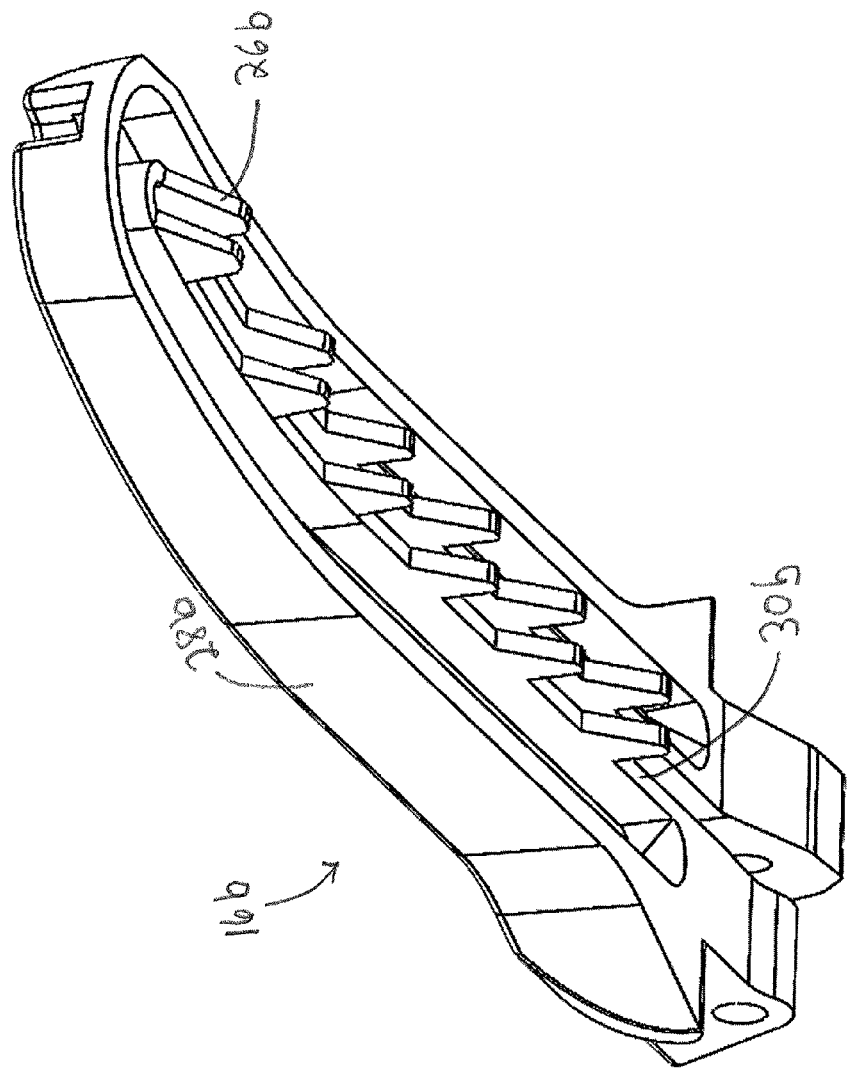
FIG. 3A is a perspective view of an upper first jaw of the end effector of FIG. 2.

FIG. 3A illustrates second jaw 16b that includes a base member 28b, which has gripping elements or teeth 26b substantially centrally disposed on a tissue contacting surface thereof. The base member 28b also has a recessed slot or channel 30b, which may be disposed between the gripping elements or teeth 26b, and extending through and at least partially along the length of the base member 28b. The slot 30b may act as a track for a cutting element, which can effect the transection of tissue.

Figure 3B:
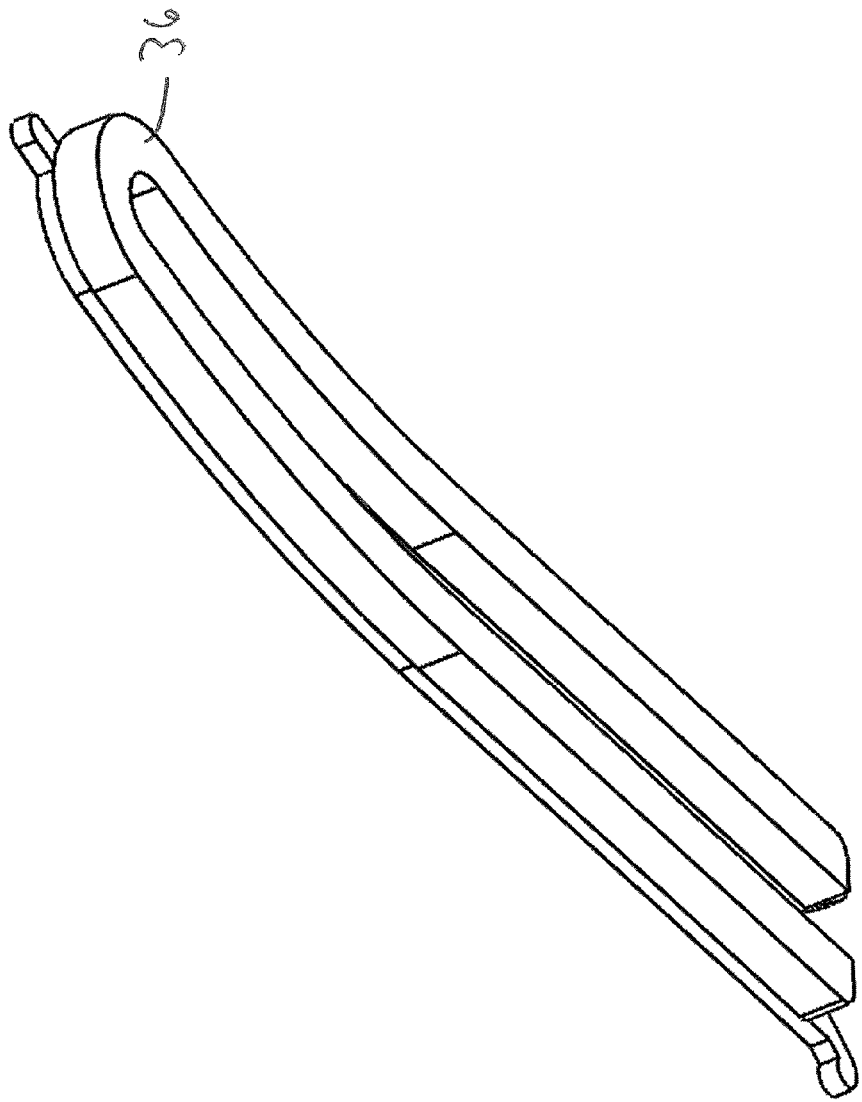
FIG. 3B is a perspective view of an insert for the upper jaw of the end effector of FIG. 2.

FIG. 3B shows an insert 36 that can be positioned in the base member 28b of the second jaw 16b. As discussed below, the insert 36 may be made of a PTC material or other material that serves as a return electrode and additionally helps control the power or energy delivered to tissue positioned between the first and second jaws 16a, 16b. In an embodiment, the PTC material may be a variably resistive body or matrix that includes a polymer such as polypropylene or a medical grade silicone polymer that is doped with conductive particles (e.g., carbon). Polymer PTC materials, as a person skilled in the art will appreciate, are over current protection devices that will "trip" and become resistant when a selected trip current is exceeded or upon reaching a selected elevated temperature.

Figure 3C:
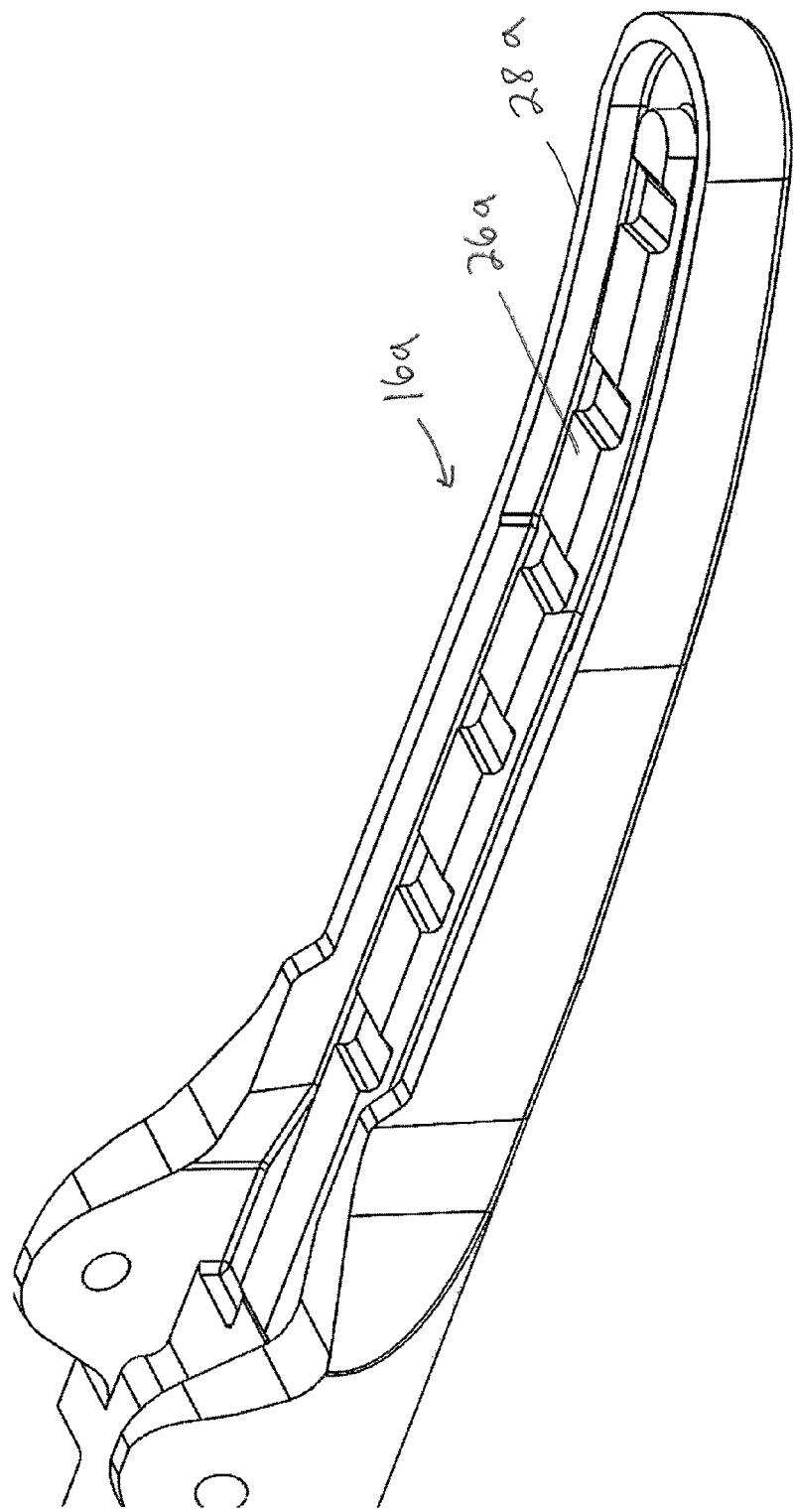
FIG. 3C is a perspective view of the lower second jaw of the end effector of FIG. 2.
Figure 3D:
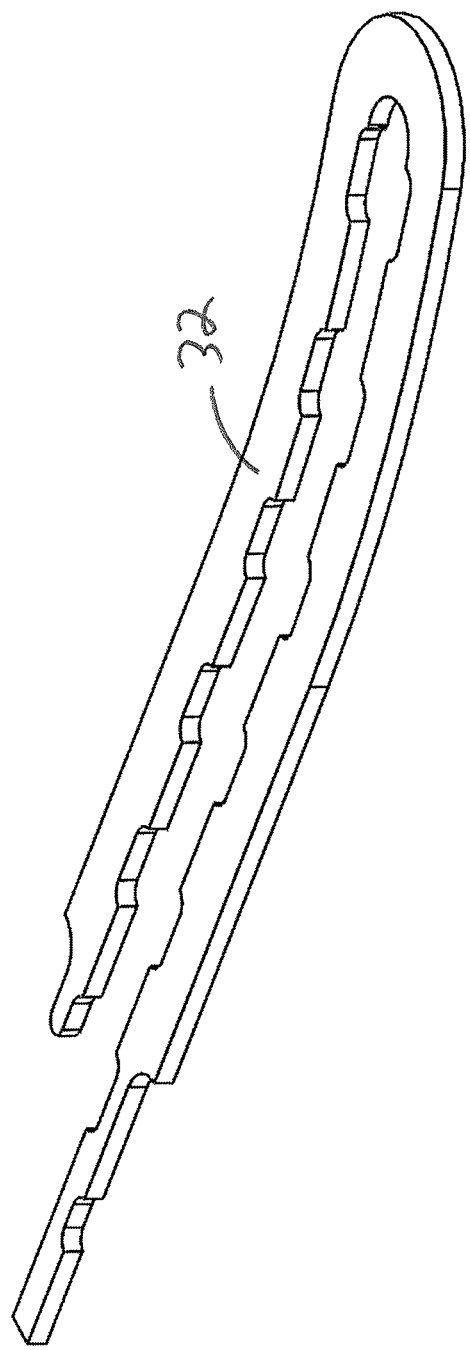
FIG. 3D is a perspective view of an electrode to be mounted on the lower jaw of the end effector of FIG. 2.
Figure 3E:
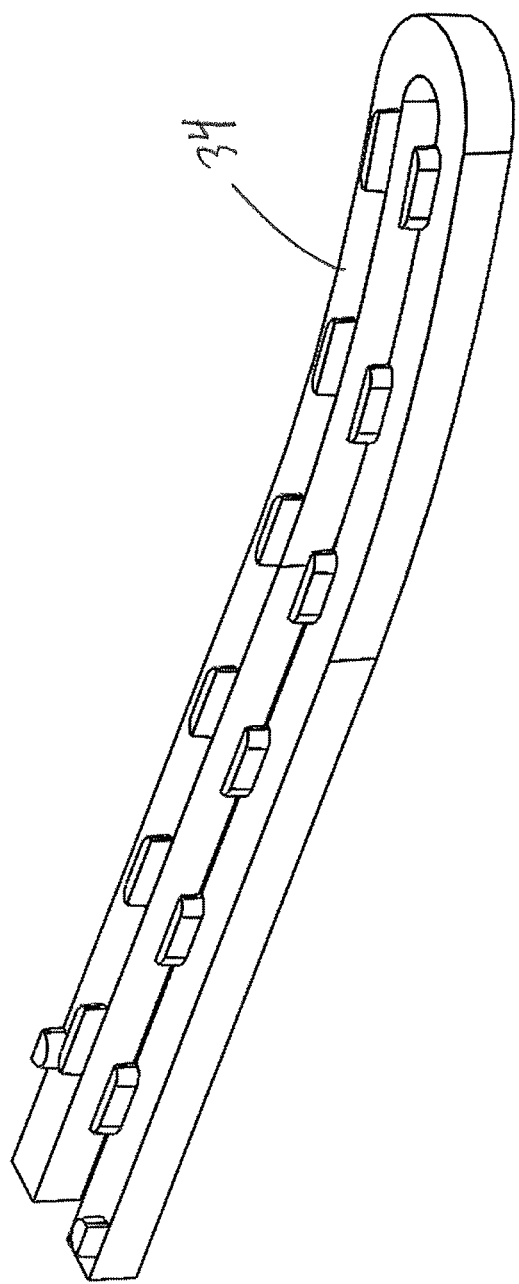
FIG. 3E is a perspective view of an insulator to be inserted in the lower jaw of the end effector of FIG. 2.

FIG. 3C illustrates a lower, first jaw 16a that includes a base member 28a with receiving elements or teeth 26a substantially centrally disposed on a tissue contacting surface thereof. Teeth 26a may be complementary to the gripping elements or teeth 26b formed on the upper, second jaw 16b. A channel 30a, as shown in FIG. 2, may extend at least partially along the length of the base member 28a to act as a track for a cutting element during the transection of tissue. As shown in FIG. 2 and FIG. 3D, an energy delivering electrode 32 is mounted on the base member 28a and forms the first tissue engaging surface 18a. As shown in FIG. 2 and FIG. 3E, the base member 28a also includes an insulator 34 such as a ceramic insert upon which the energy delivering electrode 32 is mounted to electrically insulate the base member 28a and the gripping elements or teeth from energy delivering electrode 32. The energy delivering electrode 32 may be coupled to a second polarity such that the end effector can operate in a bipolar mode to treat tissue.

FIG. 4 shows a perspective view of another example of an end effector 114 having a first jaw 116a and a second jaw 116b and an energy delivering electrode 132 forming a portion of the first tissue engaging surface 118a of the first jaw 116a. As shown, the electrode 132 extends along the length of jaw 116a. The electrode 132 can occupy substantially the entire width of jaw 116a, except for the portion of the jaw occupied by teeth 126a and channel 130a. A person skilled in the art will appreciate that the length and width of the electrode 132 can vary such that it can span substantially less than the length of jaw 116a and a lesser portion of the width of jaw 116a. A person skilled in the art will appreciate that the dimensions of the electrode 132 will vary depending on the size of the end effectors and the intended use of the surgical tool. Generally, the electrode 132 can have a length L in the range of about 15 mm to about 45 mm. The electrode 132 may have a total width W in the range of about 2 mm to about 12 mm (not including the distance across channel 130a). The distance or width D across each side of the electrode 132 (from the edge to the channel 130a) may be at least 1 mm. In an embodiment, the distance of width D is about 1 mm to about 6 mm. The thickness H of the energy delivering electrode 132 may likewise vary depending upon the size of the end effectors and the intended use of the surgical tool. Although the electrode 132 may be of any desired thickness, by way of example, however, the electrode 132 may have a thickness in the range of about 0.025 mm to about 0.25 mm, a length in the range of about 15 mm to 45 mm and a width in the range of about 2.7 mm to 12 mm. In one embodiment, the electrode 132 has a length L of about 15 mm and a total width W (not including channel 130a) of about 2.7 mm, and a thickness H of about 0.25 mm. In another embodiment, the electrode 132 has a length L of about 45 mm, a total width W of about 12 mm, and a thickness of about 0.25 mm. The energy delivering electrode can have a substantially uniform thickness throughout its width and length, or the thickness can vary along the length of the electrode. The electrode can have any desired dimensions. Also, an entire jaw can be an electrode.

FIGS. 5-8 illustrate an electrode, and portions of end effectors having such an electrode, constructed in accordance with the present disclosure, in which the electrode has a selected pattern of varying conductivity.

The energy delivering electrode as described herein is formed of an effectively conductive material. For example, the energy delivering electrode may include a substrate having a conductive coating thereon or the energy delivering electrode can be formed of a polymer substrate that includes a metal. As noted above, the electrode can be constructed with a varying pattern of conductivity, which is selectively developed to ensure the proper and desired application of energy to tissue to achieve a desired result. For example, the pattern may be selected to control energy density along the energy delivering electrode in a desired manner so as to obtain a consistent tissue seal along the length of the first tissue engaging surface when tissue is clamped between the first jaw and the second jaw and energy is applied to the first tissue engaging surface.

Figure 5:
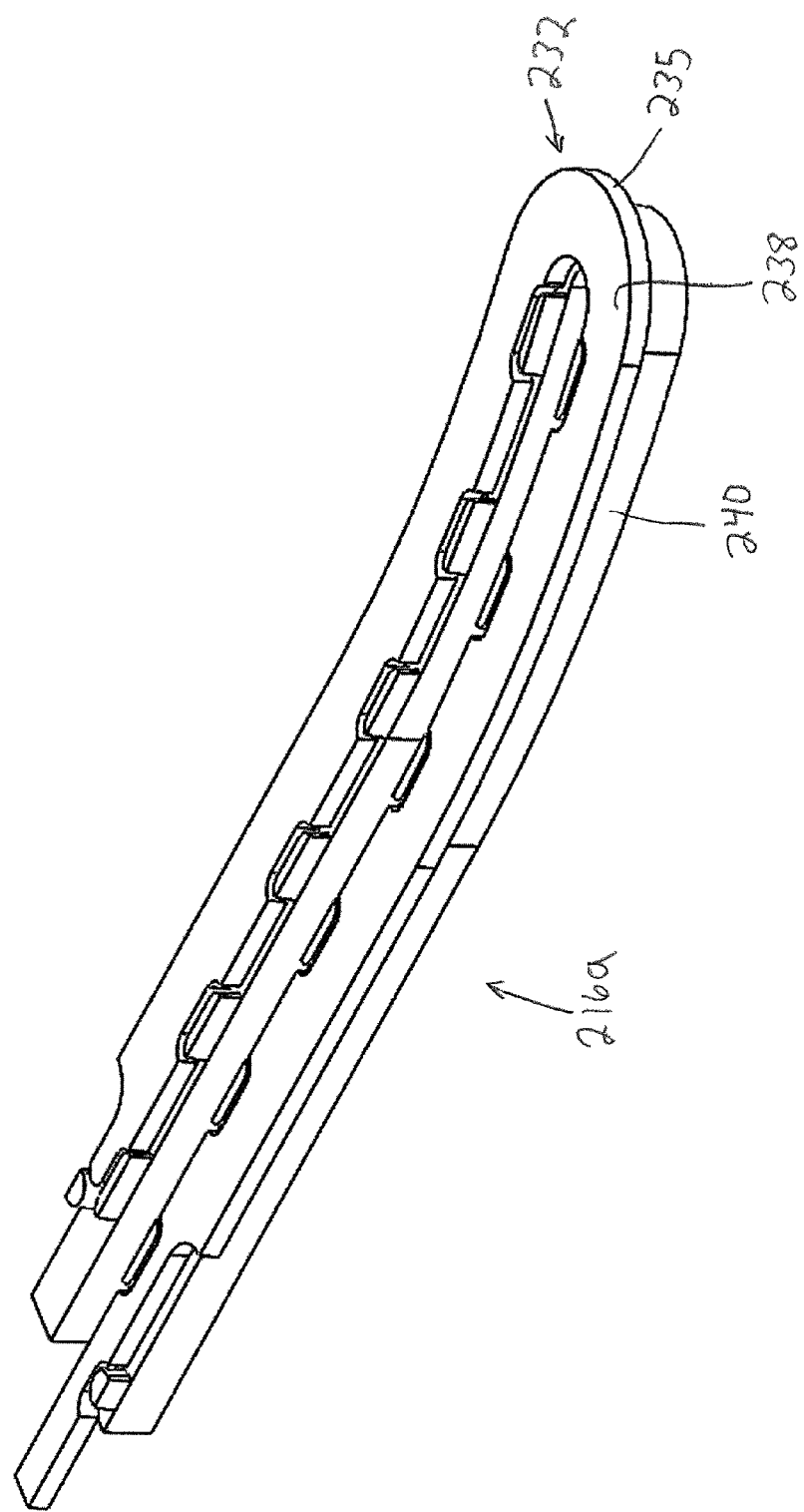
FIG. 5 is a perspective view of a coated electrode.

FIG. 5 shows a portion of an exemplary first jaw 216a with an energy delivering electrode 232 positioned on an optional conductive base 240. The energy delivering electrode 232 includes a conductive coating such as a metal film 238 that is mounted upon a substrate 235, which may be a polymeric material. While the energy delivering electrode 232 may itself be connected to a conductive lead in electrical communication with an energy source to provide the necessary conduction of current, a secondary conductive path may optionally be used. That is, because the metal film is very thin, its resistance may be high and it may be desirable to have multiple contact points between the electrode and a conductive lead. As shown in FIG. 5, energy delivering electrode 232 may be mounted on a conductive plate, such as conductive base 240, (e.g., by soldering) to provide a greater conductive path as a result of contact with the conductive plate along the entire surface of the electrode. The conductive plate may be a solid conductor formed of any desired conductive material that is suitable for biomedical applications. In one example, the conductive plate 240 may be formed of stainless steel. In another example, the conductive plate 240 can be formed of aluminum, copper, phosphor bronze, or any another conductive material. The conductive plate 240 can include more than one conductive material. For example, the conductive plate 240 can include a gold plated stainless steel. In the event that a conductive plate 240 is used, a person skilled in the art will appreciate that it may be connected to a lead that is coupled to a power source such as an RF power source.

An energy delivering electrode, such as electrode 232 having selectively varying conductive properties, may be made by depositing a material including a metal on a polymer substrate to form a conductive film and subsequently subjecting the film-substrate assembly to an ion beam metal mixing process to disperse metal ions throughout the substrate in a desired pattern, such as density, to create the desired pattern of conductivity in the electrode.

The polymer substrate may be formed from any material that is or includes a polymer and that is acceptable for biomedical applications. In some embodiments, the polymer may be a thermoplastic. Suitable polymers include, but are not limited to, acrylonitrile-butadiene-styrene (ABS), polyacrylonitrile, polyamides, polyimides, polycarbonates, polybutylene terephthalate, polyester, polyethylene, polymethylmethacrylate (PMMA), polyoxymethylene, polyphenylene oxide, polypropylene, polyvinyl chloride (PVC), polystyrene, polysulfone, polytetrafluorethylene (PTFE), polyurethanes, and polyether ether ketone (PEEK). The polymer may be used alone or mixed with other materials prior to forming the electrode to increase the current carrying capacity of the electrode. For example, the polymer may be mixed with carbon black or carbon fiber prior to electrode formation, which may be effected by a variety of techniques, including injection molding, extrusion, and compression molding.

A variety of conductive metals and metal alloys can be deposited on the substrate by suitable processes including, but not limited to, thermal evaporation and vapor deposition. In an embodiment, a metal is applied by a vapor deposition process. The metal can include, but is not limited to, antimony, tin, silver, gold, aluminum, nickel, nickel chromium, copper nickel chromium, titanium, or any other desired conductive metal or metal alloy. One or more metals may be applied to the polymer substrate. In certain embodiments, the metal is tin, antimony, or an alloy of tin and antimony. The metal particles deposited on the substrate may have any suitable particle size. For example, the metal particles may be about 10 nm to about 150 nm in diameter.

The metal film may be of any desired thickness that is suitable to achieve the desired conductive properties. Typically, however, the thickness of the film is in the range of about 0.1 μm to about 50 μm. In an embodiment, the thickness of the film is in the range of about 40 μm to about 50 μm. A person skilled in the art will appreciate that an increased thickness may be desired to increase current carrying capacity of the electrode.

The metal applied as a film on the substrate may be selected based on the resistivity of the metal. In an embodiment, the metal applied to the polymer substrate may have a resistivity in the range of about $1 \times 10^{-8}$ Ω·m to about $5 \times 10^{-8}$ Ω·m. For purposes of comparison, Table 1 shows electrical resistivity values of various metals that can be applied to the polymer substrate by a vapor deposition process:

TABLE 1

| Material | Resistivity ($\times 10^{-8}$ Ω · m) |
|---|---|
| Stainless Steel | 69-80 |
| Silver | 1.59 |
| Copper | 1.68 |
| Gold | 2.44 |
| Aluminum | 2.82 |
| Molybdenum | 5.3 |
| Nickel | 6.99 |
| Tin | 10.9 |
| Titanium | 42 |
| Antimony | 40 |

Following deposition of the metal film, the metal is mixed in the polymer substrate to achieve a desired level of conductivity, which may vary at different locations on the electrode. A person skilled in the art will appreciate that the energy delivering electrode may be formed to have a pattern of conductivity that can vary in any number of ways. For example, the energy delivering electrode made of the polymer substrate including a metal can have conductivity ranging from non-conductive or high resistivity to conductive or low resistivity.

The surface of the tissue engaging surface of the energy delivering electrode can include some portions that are conductive and other portions that are non-conductive or less conductive. The electrode may have any desirable conductivity values that effect energy density control when energy is applied to the electrode during a tissue sealing process. For example, the portions of the energy delivering electrode that are conductive may include a range of conductivity. In certain embodiments, the conductivity may range from about $1 \times 10^8$ S/m to about $10 \times 10^{-23}$ S/m. In other embodiments, the conductivity may range from about $6 \times 10^8$ S/m to about 1 S/m.

Figure 6:
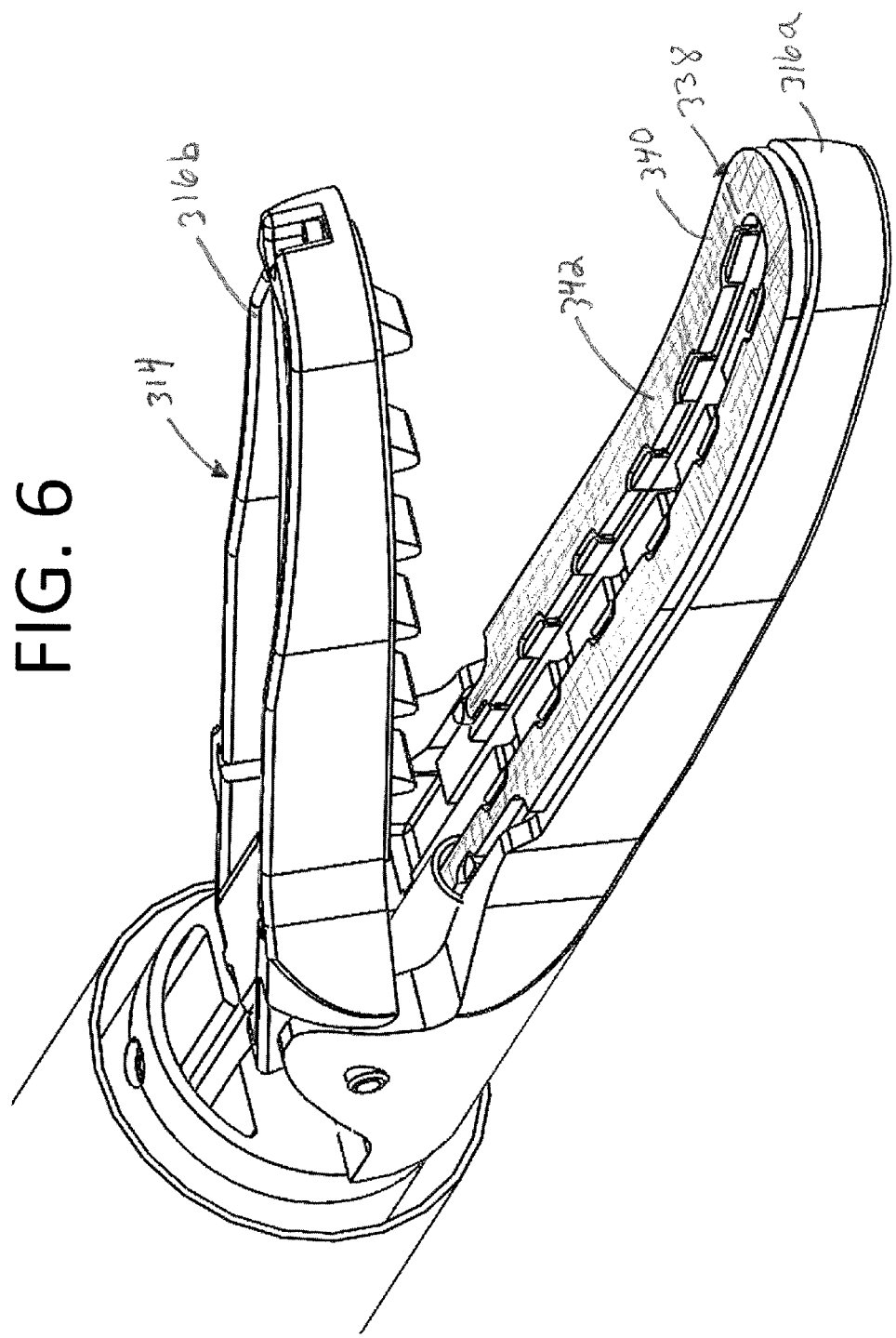
FIG. 6 is a perspective view of an end effector having a pattern of conductivity on an electrode.

The surface or volume of the energy delivering electrode may have any desired percentage of conductivity (i.e., the percent of the surface or volume that includes conductive material) that will be effective in controlling energy density during a tissue sealing process. The surface or volume of the energy delivering electrode may have any desired percentage of high conductivity (i.e., the percent of the surface or volume that includes areas of higher conductivity relative to other portions of the electrode) that will be effective in controlling energy density during a tissue sealing process. The higher conductivity area may have a conductivity between about $1 \times 10^6$ S/m and about $1 \times 10^8$ S/m. The lower conductivity may have a conductivity of about $10^{-24}$ to about 1. In one example, at least about 50% of the surface or volume of the energy delivering electrode may have higher conductivity. In one embodiment, less than about 50% of the surface or volume of the energy delivering electrode may have higher conductivity. In another embodiment, about 50% of the surface or volume of the energy delivering electrode may have a higher conductivity. FIG. 6 shows an embodiment of an end effector 314 having a lower jaw 316a and an upper jaw 316b, where the lower jaw 316a includes an electrode 332 formed by a conductive metal film 338 of the type described herein where about 50% of the metal film is of higher conductivity. In the illustration of FIG. 6, regions of higher conductivity are represented by the white areas 342 and regions of lower conductivity are represented by dark areas 340. A person skilled in the art will appreciate that the dark areas 340 can represent areas that are generally of lower conductivity than the white areas 342.

Figure 7:
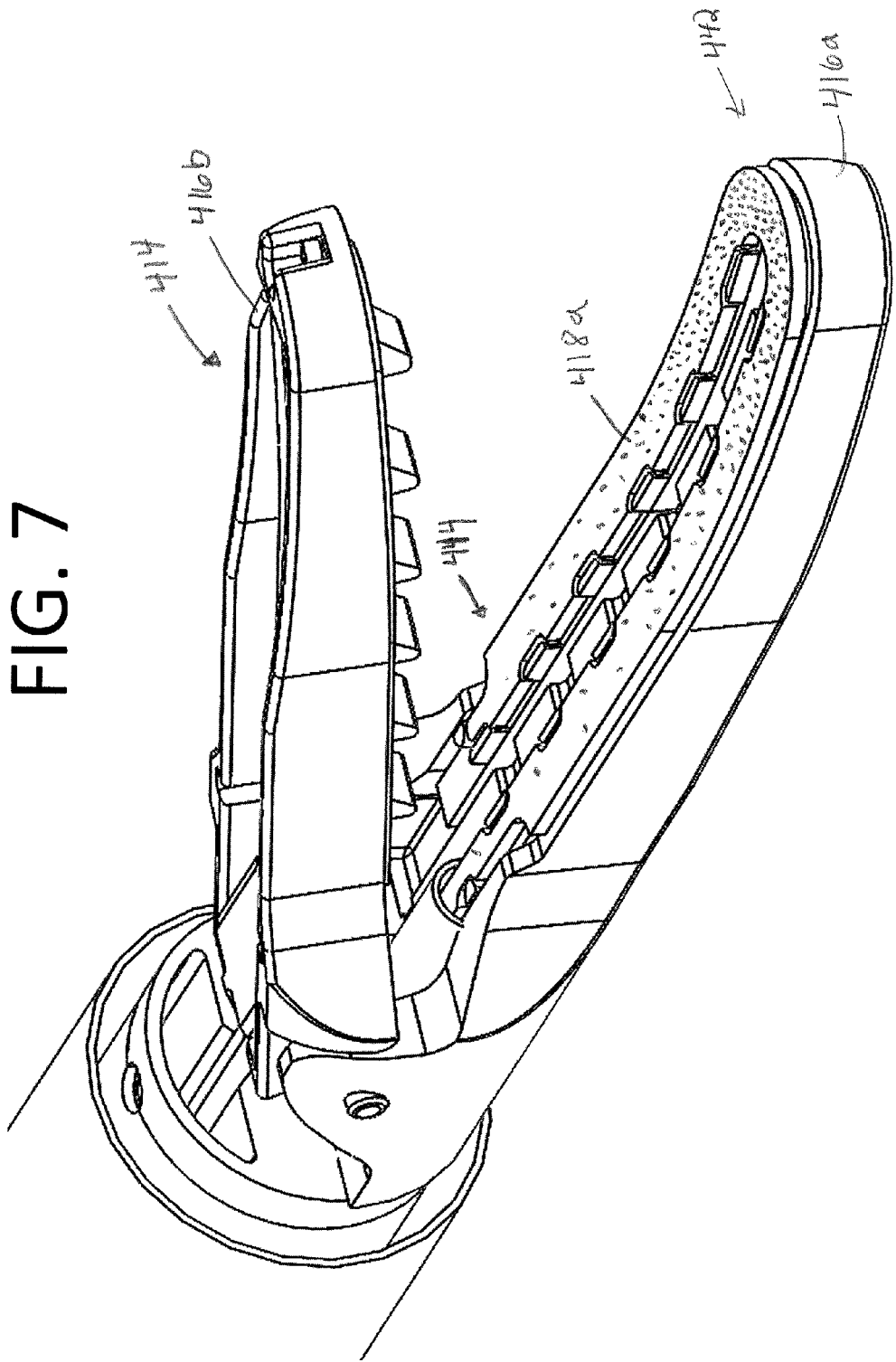
FIG. 7 is a perspective view of another embodiment of an end effector having a continuous pattern of conductivity on an electrode.

The selected pattern of conductivity on the energy delivering electrode can vary in a number of ways. As explained below, the energy delivering electrode can have one or more discrete regions of conductivity or a continuous pattern of varying conductivity. The conductivity on the energy delivering electrode may be in the form of a gradient, such as depicted in FIGS. 7 and 8, or the changes can be stepped or very distinct. The pattern may include at least one conductive trace. Also, the areas between the higher and lower areas of conductivity described above can have a transition in conductivity from the higher to lower conductivity values. The transition in conductivity may be linear, logarithmic, exponential, step function, oscillatory, or any conceivable pattern of dots, lines, hatching, grids, or other shapes.

In some embodiments where the selected pattern is a gradient of conductivity, the gradient can extend from a distal end to a proximal end of the energy delivering electrode. FIG. 7 illustrates an embodiment of an end effector 414 having a first jaw 416a and a second jaw 416b. The first jaw 416a includes a first tissue engaging surface 418a where a selected pattern of varying conductivity is a gradient from the distal end 442 to the proximal end 444 of the tissue engaging surface 418a. FIG. 7 shows an electrode 432 with a gradient where the conductivity is greater at the proximal end 444 and less at the distal end 442 of the tissue engaging surface 418a. The conductivity may be reduced in the distal direction proportionally to the width of the electrode. In other embodiments, the distal end of the first tissue engaging surface may be more conductive than the proximal end of the energy delivering electrode and thus the conductivity decreases from the distal end to the proximal end.

In another embodiment where the selected pattern is a gradient of varying conductivity, the conductivity can vary from the longitudinal axis of the energy delivering electrode to the outer edges of the energy delivering electrode. FIG. 8 shows an embodiment of an end effector 514 having a first jaw 516a and a second jaw 516b where the first jaw 516a includes a tissue engaging surface 518a that includes an electrode 532 with a gradient of conductivity that extends radially from the longitudinal axis $L_1$ of the electrode to the outer edges 546 of the electrode. The conductivity is the lowest closest to the longitudinal axis of the end effector and increases as it extends radially from the longitudinal axis towards the edges of the electrode.

In one embodiment, the conductivity may be higher along the longitudinal axis of the energy delivering electrode and decrease radially towards the edges of the electrode. For example, the edges may have a resistivity that is about 10× higher (e.g., about $75 \times 10^{-8}$ Ω·m) than the area closer to the longitudinal axis (or slot for the cutting element) which may be about $10 \times 10^{-8}$ Ω·m. This pattern can be effective to reduce thermal spread on the tissue by containing the majority of energy central to the longitudinal axis.

An energy delivering electrode having such selected regions or patterns of varying conductivity described above may be formed by any suitable process such as, for example, a metal mixing process that varies the concentration or density of the metal in or on the surface of the polymer substrate. In an embodiment, the metal mixing process involves applying an ion beam, such as a heavy element ion beam, to a metal film deposited on a polymer substrate. The ion beam disperses the metal ions in the polymer substrate to vary the conductivity, as described below. Ion beams may be used for inducing large changes in conductivity of the substrate. Suitable ion beam processes include, for example, those set forth in Stephenson, et al., "A Tunable Metal-Organic Resistance Thermometer," ChemPhysChem, 2011, 12, 116-121, which is incorporated herein by reference in its entirety. Any ion source can be used to apply the ion beam including, for example, hot cathode, cold cathode and plasmatron ion sources.

Many materials can be used in an ion beam process for forming the energy delivering electrode. The ion beam may include ions of one or more metals. The ion beam may include ions of metals such as, but not limited to, antimony, aluminum, gold, cobalt, chromium, iron, gallium arsenide, gallium nitride, germanium, molybdenum, niobium, osmium, palladium, platinum, rhodium, ruthenium, rhenium, silicon, silicon nitride, silicon oxides, tin, titanium oxides, or tungsten. In one embodiment, a 19:1 Sn/Sb (tin/antimony) alloy can be deposited as a thin metal film by a process such as thermal evaporation and then implanted via an ion beam including $Sn^+/Sn^{++}$. In an embodiment, argon ($Ar^+$), krypton ($Kr^+$), chlorine ($Cl^+$), bromine ($Br^+$), hydrogen bromide ($HBr^+$), or nitrogen ($N^+$) ions may be used.

One or more parameters of the ion beam can be varied as the ion beam is applied to the metal film to form the selected pattern of varying conductivity. For example, the dose or concentration of the ions in the ion beam may be varied as the ion beam is applied to the metal film. The concentration of ions may range from about $1 \times 10^{15}$ ions cm$^{-2}$ to about $1 \times 10^{17}$ ions cm$^{-2}$. In an embodiment, the concentration of the ions is about $1 \times 10^{15}$ ions cm$^{-2}$ to about $1 \times 10^{16}$ ions cm$^{-2}$. The energy of the ion beam may be varied as the ion beam is applied to the metal film. The energy of the ion beam may vary between about 10 kV to about 500 kV. In an embodiment, the energy of the ion beam is about 10 kV to about 20 kV. In an embodiment, the concentration of the ions is $1 \times 10^{15}$ ions cm$^{-2}$ and the energy of the ion beam is 10 kV.

A number of patterns and ranges of conductivity, including those described above, may be created by varying these and other parameters of the ion beam. Also, it will be appreciated that the concentration of ions or energy of the ion beam may be increased or decreased to adjust the conductivity of the substrate. For example, a lower concentration of ions or lower energy of the ion beam will result in less mixing of the metal in the polymer substrate and lower conductivity.

The parameters for the ion beam deposition may vary depending on the thickness of the metal film on the substrate and the desired resistance. For example, variations in dose, concentration, and metal film thickness described in Stephenson, et al. may be applied to create the selected pattern of varying conductivity. In one embodiment, with a metal film that is approximately 15 nm in thickness, a low resistance film can be achieved by using a dose of $1 \times 10^{15}$ ions cm$^{-2}$ and energy of 20 KeV. The resistance can then be increased by a factor of 10 by reducing the energy to 10 KeV. In one embodiment, a PEEK substrate can be coated by vapor deposition of Sn/Sb to form a film of metal. The metal can be implanted in the substrate by application of an Sn+/Sn+ ion beam with a starting energy of 20 keV and dose of $1 \times 10^{15}$ ions cm$^{-2}$ and a final energy of 10 keV and dose of $1 \times 10^{15}$ ions cm$^{-2}$ where the energy decreases linearly from a starting point to an ending point on the electrode.

A method of making an electrode for a surgical tool described above generally includes depositing a film comprising a metal on a polymer substrate, and applying an ion beam to the film in a desired manner to form a selected pattern of varying conductivity. In an embodiment, a single polymer substrate is formed on a tissue engaging surface of a surgical tool, and the polymer substrate is treated by a metal mixing method where a thin metal film is deposited on the surface of a polymer substrate and mixed into the polymer substrate by a heavy metal ion beam.

As described above, the metal may be applied to the substrate using a thermal evaporation process, vapor deposition process, or any other suitable process. The selected pattern of conductivity may be formed by varying the amount of ions in the ion beam, the energy of the ion beam, or a combination thereof, as the ion beam is applied to the film of metal. These and other parameters for the ion beam deposition may vary depending on the thickness of the metal film on the substrate and the desired resistance.

The selected pattern of varying conductivity formed by the method described above may include a discrete region or continuous pattern of varying conductivity. The method may include creating a gradient of conductivity. For example, the ion beam process may be applied to form a gradient that extends from either a distal end to a proximal end of the energy delivering electrode or extends from the longitudinal axis to the outer edges of the energy delivering electrode, as shown in FIGS. 7 and 8, respectively.

The method provided herein allows for precise control over the amount of metal mixed in the polymer. Accordingly, a wide range of conductivity ranging from metal/superconductor to insulator can be achieved across the electrode by varying parameters of the ion beam process such as the ion dose and beam energy. The pattern of varying conductivity can be selected to control the energy density in a near continuous manner across an electrode so as to obtain a consistent tissue seal.

The devices herein can be used to perform a surgical procedure in which tissue is grasped and transected, and sealed using applied energy. A person skilled in the art will appreciate that the procedure is ideally a minimally invasive procedure, but can alternatively be an open surgical procedure. The devices herein can also be used for robotic-assisted minimally invasive or open procedures. The surgical device can apply energy, e.g., RF current, to tissue disposed between the jaws prior to, during, and/or after transection of the tissue.

A person skilled in the art will appreciate that any of the embodiments discussed above can be combined with one another in a variety of manners. Furthermore, a device could be provided that allows a user to select a particular mode that the device operates in, or what features are provided.

The devices disclosed herein can be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

Although particular embodiments have been described above in detail, it will be understood that this description is merely for purposes of illustration. Specific features are shown in some drawings and not in others, and this is for convenience only and any feature may be combined with another. Also, elements or steps from one embodiment can be readily recombined with one or more elements or steps from other embodiments. Further, one skilled in the art will appreciate further features and advantages of the devices and methods based on the above-described embodiments. Accordingly, the device and methods are not to be limited by what has been particularly shown and described. Finally, all publications and references cited herein are expressly incorporated herein by reference in their entirety.

What is claimed is:

1. A method of making an electrode for a surgical tool, where the electrode has a selected pattern of varying conductivity, the method comprising:
depositing a film comprising a metal on a polymer substrate,
applying an ion beam to the film, and
after beginning the application of the ion beam to the film, forming the selected pattern of varying conductivity by varying the applied ion beam by changing a concentration of ions in the ion beam, changing an energy of the ion beam, or a combination thereof, wherein the selected pattern comprises a gradient of conductivity that extends from a distal end to a proximal end of the energy delivering electrode or extends radially from a longitudinal axis to outer edges of the energy delivering electrode.

2. The method of claim 1, wherein the film is deposited using a vapor deposition process.

3. The method of claim 1, further comprising varying a thickness of the film during the deposition of the film.

4. The method of claim 1, wherein the film is deposited using a thermal evaporation process.

5. The method of claim 1, wherein the selected pattern comprises one or more discrete regions or a continuous pattern of varying conductivity.

6. The method of claim 1, wherein the applied ion beam is varied depending on a thickness of the metal on the polymer substrate and a desired resistance.

7. A method of making an electrode for a surgical tool, where the electrode has a selected pattern of varying conductivity, the method comprising:
depositing a film comprising a metal on a polymer substrate,
applying an ion beam to the film, and
after beginning the application of the ion beam to the film, forming the selected pattern of varying conductivity by varying the applied ion beam by changing a concentration of ions in the ion beam, the selected pattern comprising a gradient of conductivity that extends from a distal end to a proximal end of the energy delivering electrode or extends radially from a longitudinal axis to outer edges of the energy delivering electrode.

8. The method of claim 7, wherein the film is deposited using a vapor deposition process.

9. The method of claim 7, further comprising varying a thickness of the film during the deposition of the film.

10. The method of claim 7, wherein the film is deposited using a thermal evaporation process.

11. The method of claim 7, wherein the selected pattern comprises one or more discrete regions or a continuous pattern of varying conductivity.

12. The method of claim 7, wherein the applied ion beam is varied depending on a thickness of the metal on the polymer substrate and a desired resistance.

* * * * *